United States Patent
Fritz

(10) Patent No.: US 9,649,145 B2
(45) Date of Patent: May 16, 2017

(54) SUPPLY DEVICE

(75) Inventor: Martin Fritz, Tuebingen (DE)

(73) Assignee: Erbe Elektromedizin GmbH, Tuebingen (DE)

(*) Notice: Subject to any disclaimer, the term of this patent is extended or adjusted under 35 U.S.C. 154(b) by 1463 days.

(21) Appl. No.: 13/370,591

(22) Filed: Feb. 10, 2012

(65) Prior Publication Data

US 2012/0209256 A1   Aug. 16, 2012

(30) Foreign Application Priority Data

Feb. 14, 2011 (EP) .................................. 11154266

(51) Int. Cl.
 - A61B 18/22 (2006.01)
 - A61B 18/12 (2006.01)
 - A61B 17/3203 (2006.01)
 - A61B 18/02 (2006.01)
 - A61B 18/00 (2006.01)

(52) U.S. Cl.
CPC ...... *A61B 18/1206* (2013.01); *A61B 17/3203* (2013.01); *A61B 18/02* (2013.01); *A61B 2018/00684* (2013.01)

(58) Field of Classification Search
USPC ................. 606/20, 41, 169; 607/59
See application file for complete search history.

(56) References Cited

U.S. PATENT DOCUMENTS

| | | | |
|---|---|---|---|
| 5,423,000 A * | 6/1995 | Kimura | G06F 9/46 713/1 |
| 6,529,934 B1 * | 3/2003 | Kawamura | G06F 9/4875 709/202 |
| 2004/0243025 A1* | 12/2004 | Peles | A61H 1/0277 601/5 |
| 2006/0257836 A1* | 11/2006 | Humphries et al. | 434/262 |
| 2006/0259259 A1* | 11/2006 | Rozenboim | G05B 19/4184 702/83 |
| 2007/0179495 A1* | 8/2007 | Mitchell et al. | 606/41 |
| 2009/0149917 A1 | 6/2009 | Whitehurst | |
| 2010/0125292 A1* | 5/2010 | Wiener et al. | 606/169 |
| 2010/0179535 A1* | 7/2010 | Podhajsky | A61B 18/1206 606/34 |
| 2011/0172564 A1* | 7/2011 | Drew | A61B 5/061 600/587 |

FOREIGN PATENT DOCUMENTS

| | | |
|---|---|---|
| DE | 10 2009 042 428 | 3/2011 |
| JP | 2009-524495 A | 7/2009 |
| WO | WO 96/13216 | 5/1996 |

* cited by examiner

Primary Examiner — Edward Moran
Assistant Examiner — Natasha Patel
(74) Attorney, Agent, or Firm — Blank Rome LLP

(57) ABSTRACT

A supply device for a surgical apparatus for operating a surgical instrument that includes a control unit for controlling the surgical instrument, a memory unit for storing configuration data, and a mediating unit for allocating an adjustment value to a mathematical function to obtain a scaling factor, and methods of using such a supply device.

13 Claims, 2 Drawing Sheets

SUPPLY DEVICE

CLAIM OF PRIORITY

This application claims priority to European patent application number EP 11 154 266.8, filed Feb. 14, 2011, the entirety of which is hereby incorporated by reference.

FIELD OF THE INVENTION

Embodiments of the present invention relate to a supply device for a surgical apparatus for operating at least one surgical instrument, as well as to a method for controlling such a supply device.

BACKGROUND

Several forms of surgery and medical treatment utilize specialized surgical instruments that require a supply of power or material to operate. For example, such specialized surgical instruments include an electrosurgical instrument, cryosurgical instrument or waterjet instrument.

Electrosurgery is the application of a high-frequency electric current to biological tissue as a means to cut, coagulate, desiccate, or fulgurate tissue. Its benefits include the ability to make precise cuts with limited blood loss. In electrosurgical procedures, the tissue is heated by an electric current manipulated using an electrosurgical instrument, which must be supplied with electrical power. Electrosurgical devices may be used for the cauterization of tissue in some applications or, more often, in dermatological, gynecological, cardiac, plastic, ocular, spine, ENT, maxillofacial, orthopedic, urological, neuro- and general surgical procedures, as well as certain dental procedures. Electrosurgery is performed using an electrosurgical generator (also referred to as power supply or waveform generator) and a handpiece, i.e., the electrosugical instrument, including one or several electrodes, sometimes referred to as an RF Knife.

Cryosugery is a technique employing the use of low temperatures to destroy cells and abnormal or diseased tissue. The low temperatures are applied using a cryosurgical instrument, which must be supplied with cryogenic material, e.g., liquid nitrogen. Such cell or tissue death is usually by plasma membrane and protein disruption via physical and osmotic damage when ice crystals form within the cytoplasm of the cells. Warts, moles, skin tags, solar keratoses, Morton's neuroma and small skin cancers, for example, are candidates for cryosurgical treatment. Several internal disorders are also treated with cryosurgery, including, for example, liver cancer, prostate cancer, lung cancer, oral cancers, cervical disorders and, commonly in the past, hemorrhoids. Soft tissue conditions such as plantar fasciitis and fibroma can be treated with cryosurgery. Generally, damaged or diseased tissues that can be reached by the cryoprobes used as surgical instruments during an operation are treatable.

Waterjet surgery is a minimally traumatic surgical method for dissection of tissues. For example, waterjet surgical techniques can be used in various parenchymal organs and allow highly precise parenchymal dissection while preserving blood vessels, resulting in reduced intraoperative blood loss. In such surgery, a waterjet surgical instrument is used in the process and must be supplied with water.

Supply devices used for operating a surgical instrument, such as, the electrosurgical, cryosurgical or waterjet surgical instruments discussed above have included a control unit for controlling the instrument, as well as a memory unit for storing configuration data describing a finite-state machine (also referred to as a finite-state automaton), i.e., a state automaton featuring a plurality of states. Such a control unit is configured such that it reads in the configuration data, translates the finite automaton into a control program and controls at least one instrument consistent with the control program. A surgical instrument that is connected to a surgical apparatus can thus be programmed in a simple manner, and a verification of the accuracy of programming is ensured rapidly and efficiently with the use of a state automaton.

Considering known supply devices, a framework program or a framework within such a supply device is provided, which allows the control program for the instrument to be read in and translated in the form of a state automaton. The term "state automaton" is used herein as a term synonymous with a finite-state automaton or a finite-state machine, i.e., generally representing a model of a behavior, consisting of states, state transitions and actions. Usually, the above-addressed framework program need not be modified to further develop the functionality of the supply device. The actual control of the instruments takes place with the use of the state automaton that is described by configuration data. It is very easy to validate if a state automaton is correct. Preferably, deterministic automatons are used, so that it is easy to verify whether the automaton functions correctly. Due to the use of state automatons, it is possible to minimize the amount of work in the process of developing new control and regulating algorithms, whereby the safety of the patient and of the personnel operating the supply device is ensured at all times.

Considering supply devices of the known type, there is the problem that, while the control program is running, for example, for changing the intensity of a tissue effect and, in particular, for changing the voltage, a current or an output, it is necessary—in certain situations—that a change of the default values or the adjusted values must be made at several points in the implementation of the state automaton. When conventional supply devices are used, the user must perform manual adjustments on adjustment devices such as potentiometers or the like.

However, with the use of a state automaton, such a manual adjustment of parameters is not possible due to the complexity of the system. Consequently, while the state automaton is running, a user cannot perform any manual change, for example, of the output voltage or output power or the like, by actuating an adjustment device of the surgical apparatus. Further, generating a dedicated control table for the state automaton for any possible adjustment value of the adjustment device(s) would consume an enormous amount of time and would greatly reduce the advantages of clarity and the simple maintenance of the control feature by means of a state automaton.

Another disadvantage of the known supply device is that tissue parameters and/or RF measured values affecting the state transitions of the automaton define only the implementation of the state automaton and not the intensity of individual control values. In doing so, it would be desirable that the tissue parameters and/or the RF measured values not only affect the implementation of the state automaton but, in addition, can effect a change of the control parameters such as, for example, voltage, time, current, output, etc.

Therefore, there is a need for a supply device for a surgical apparatus for operating at least one surgical instrument that allows a manual influence by the user over the control values of the state automaton while the state automaton is running and also allows a change of the control values based on tissue parameters and/or RF measured values or the like, where the values are used as conditions for the state transitions between two states of the state automaton.

SUMMARY

A supply device as a part of a surgical apparatus for operating at least one surgical instrument is disclosed. The surgical instrument can be, in particular, an electrosurgical instrument and/or a cryosurgical instrument and/or a waterjet instrument. The supply device can include a control unit for controlling the at least one surgical instrument. The supply device can also include a memory unit for storing configuration data, in particular control values such as RF voltage, output, time periods or the like, describing a state automaton having a plurality of states. The control unit of the supply device is configured so that it reads in configuration data, translates the state automaton into a program, and controls at least one surgical instrument consistent with the control program. The supply device can be characterized in that a mediating unit is provided that allocates at least one adjustment value—received during the execution of the control program—of a real or a virtual adjustment device to a mathematical function by means of which a scaling factor for a specific control value is obtained.

Consequently, the supply device can include a mediating unit that allocates a received adjustment value to a specific mathematical function. In such a configuration, the mathematical function allocates to the adjustment value a scaling factor that, in turn, is used for scaling a specific control value. In doing so, it is possible, for example, when a parameter is adjusted by a user by actuating a real adjustment device such as, for example, a potentiometer on a surgical apparatus, that a change of at least one control value, or several control values, is effected. When the control program is designed, rules are defined, such as how one or more adjustment devices (potentiometer or the like) will scale, i.e., modify, the control values of the control program. The mathematical scaling functions generate characteristic lines that can allocate a performed adjustment to several different scaling factors for several control values. Consequently, one and the same adjustment or one and the same adjustment value can generate different scaling factors for different control values. Furthermore, the disclosed supply device makes it possible that, when a jump or a state transition is performed between two states of the state automaton, a virtual or also a real adjustment device is changed based on a simple rule or a normalized measured value or a constant, i.e., based on a true state transition rule. In doing so, the rule and the normalized measured value or the constant are preferably determined at the time the control table or the state automaton is designed.

An actual adjustment device can preferably be actuated by the user of a surgical apparatus and this actual adjustment device may be an adjustment knob or a similar adjustment element. In contrast, a virtual adjustment device can be provided that does not use a manually actuatable adjustment element, but rather, is made of at least one control rule for at least one transition, i.e., at least one state transition between two states of the state automaton. The result of the control rule of the virtual adjustment device thus forms the adjustment value of the virtual adjustment device and, consequently, corresponds to the adjustment value that can be set by a user on an actual adjustment device. In both cases, the respectively obtained adjustment value can be allocated to a specific function by the mediating unit that, in turn, generates the scaling factor for a specific control value.

For safety reasons, the control values can be reduced by the scaling factors which is why the scaling factors are preferably less than 1 in such a case. Consequently, the scaling factor is used for adapting and, in particular, for reducing, any control value such as, for example, a voltage, an output, a time period or the like. The control value may be any conceivable adjustable parameter of the state automaton. The scaling factor is multiplied with the respectively allocated control value and, thus, results in a control value that is to be set, said control value being pre-specified by the control.

Preferably, several mathematical functions are allocated by a mediating unit to an adjustment value of an adjustment device, said functions being intended for generating scaling factors for the adaptation of different control values. By using different mathematical functions, it is possible in this manner to use the same adjustment value for generating different scaling factors.

The adjustment values of the actual or virtual adjustment device preferably have a value between 0 and 1 and are thus normalized to the range between 0 and 1. As a result, the values of all the adjustment devices can be uniformly and simply processed by means of the mathematical functions.

A mediating unit of the type disclosed is preferably already implemented in the control table of the state automaton and is translated by the control unit, together with the state automaton, into the control program. Preferably, the mediating unit comprises several mediators in the manner of a list, whereby each mediator allocates an adjustment value of an adjustment device to a single mathematical function, while an additional mediator of the mediating unit is able to allocate an adjustment value of the same adjustment device to another mathematical function. In this way, it is possible to assign an adjustment value of a specific adjustment device to several different mathematical functions and, consequently, generate different scaling factors for different control values based on one and the same adjustment value of an actual or a virtual adjustment device.

In order to achieve the aforementioned features, a method for generating a control program exhibiting these features is also disclosed. As discussed above, the method is used for generating a control program for a supply device of at least one surgical instrument, in particular for a supply device as disclosed. Such a method can include the following steps: (1) reading-in of configuration data that describe a state automaton displaying a plurality of states; (2) translating the state automaton displaying a plurality of states into a control program by means of a control unit; and (3) controlling the at least one surgical instrument, consistent with the control program, by means of the control unit. In accordance with the disclosed apparatus, the method can include the following additional steps: (4) receiving at least one adjustment value of a real or virtual adjustment device; (5) calculating at least one scaling factor by means of the adjustment value and at least one allocated mathematical function; and (6) changing at least one allocated control value based on the scaling factor.

Preferably, the control unit of the disclosed device searches for the receipt of an adjustment value after at least one allocated mathematical function. The calculation of the scaling factor or the multiplication of the calculated scaling factor with a control value then preferably occurs during a state transition between two states of the state automaton, where the control table is recalculated by the control unit. However, other implementations for calculating the new control value are possible.

DETAILED DESCRIPTION

Figure 1:
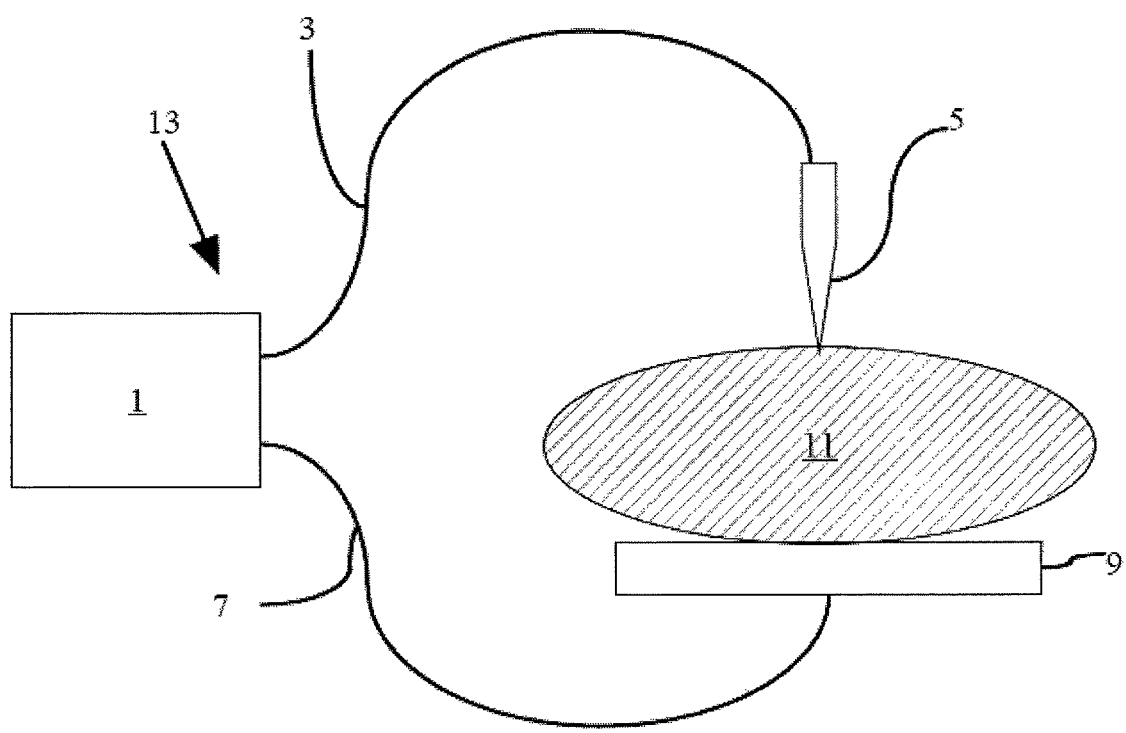
FIG. 1 shows a supply device in accordance with an exemplary disclosed embodiment having a connected exemplary electrosurgical instrument.

Referring to the figures, wherein like reference numbers denote like features, FIG. 1 shows a supply device 1 that is connected to an electrosurgical instrument 5 via a first RF lead 3. Although the embodiment illustrated in FIG. 1 relates to an electrosurgical instrument, the features can also be applied to other surgical instruments utilizing a supply device, such as, for example, cryogenic instruments and waterjet instruments, among others. FIG. 1 shows second RF lead 7 that goes to a neutral electrode 9. For the application of an RF voltage U that is made available by the supply device 1, the instrument 5 includes an active electrode. Consequently, the RF voltage U can be applied between the neutral electrode 9 and the active electrode.

As is shown by FIG. 1, the neutral electrode 9 and the active electrode of the electrosurgical instrument 5 can be used to provide an RF current I into a biological tissue 11. FIG. 1 shows a torso as one embodiment of biological tissue 11 to which a self-adhesive neutral electrode 9 is attached. The active electrode of the electrosurgical instrument 5 is used to cut or coagulate the biological tissue 11 on the other side of the torso. The instrument 5 shown by FIG. 1, used strictly as an example, is a monopolar instrument, which includes only one active electrode. However, instead of the neutral electrode 9, it is also possible to provide a bipolar instrument with two active electrodes.

The function of the supply device 1 in accordance with the invention will be explained, strictly in an exemplary manner, with reference to an electrosurgical instrument. It is understood that it is also possible that a different type of instrument 5 may be provided such as, for example, a waterjet surgical instrument or others. Usually, the supply device 1 is part of a surgical apparatus 13 that comprises adjustment devices that can be manually actuated by the user of the surgical device 13.

Figure 2:
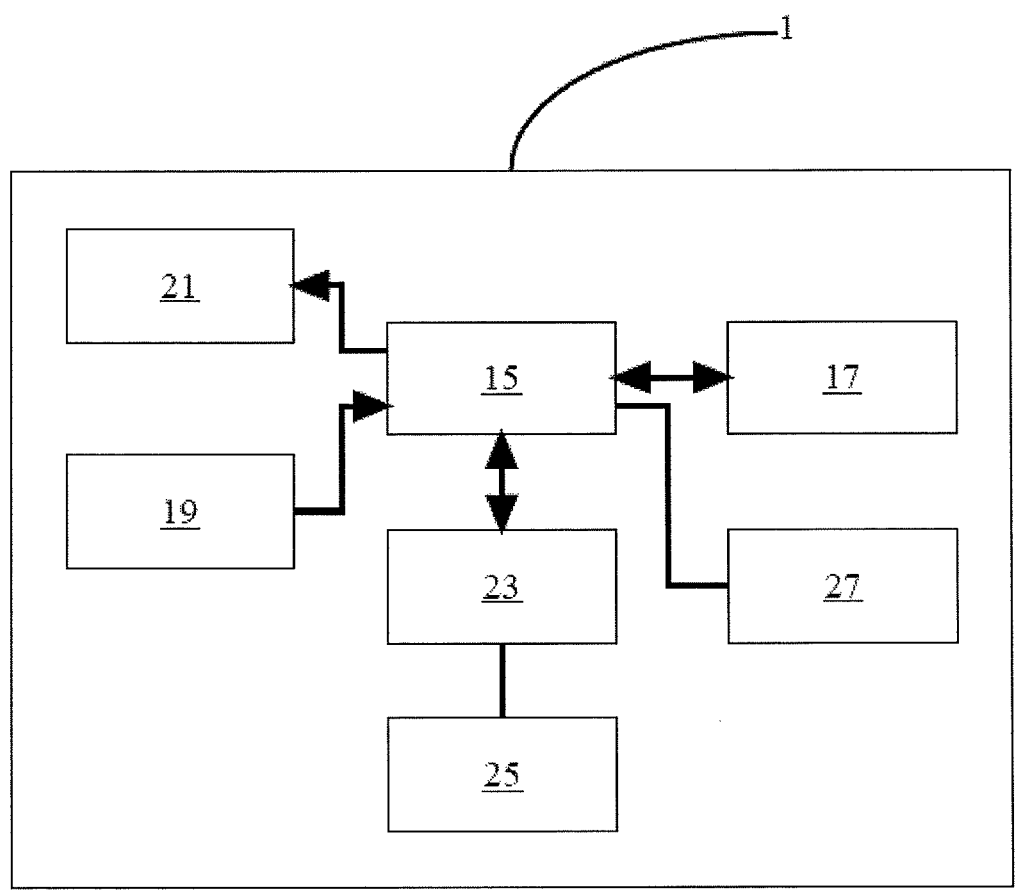
FIG. 2 shows a schematic representation of components of and exemplary supply device in accordance with an exemplary disclosed embodiment.

As is shown by FIG. 2, the supply device 1 can include a control unit 15 and an RF generator 17. The RF generator can be disposed to provide a suitable RF voltage U for the electrosurgical instrument 5 and for the neutral electrode 9. The control unit 15 controls the RF generator 17 in that the control unit outputs control signals to said generator. In addition, the control unit 15 receives sensor signals from the RF generator 17, the sensor signals can provide information regarding the state of the RF generator 17 as well as the applied RF current I or the RF voltage U. Furthermore, the control unit 15 can receive sensor signals, for example, regarding the tissue impedance R, an RF output P, or an active power factor cos Φ.

Preferably, the control unit 15 is designed to provide several different operating modes that affect, for example, the RF voltage U to be applied or the RF output P. In doing so, the control unit may offer one mode for coagulating and an additional mode for cutting tissue. Furthermore, additional modes for different electrosurgical instruments 5, for example for monopolar or bipolar instruments, or for different tissue types (liver tissue or muscle tissue) can be made available.

The supply device 1 can include an input unit 19 that is able to receive inputs from a user of the electrosurgical instrument 5. Preferably, the input unit 19 is implemented as an actual adjustment device in the form of, e.g., rotating knobs or push buttons on the surgical apparatus 13 for actuation by a user. Consequently, the user can select a specific operating mode via the input unit 19 and activate the control unit 15 such that the RF generator 17, and thus the electrosurgical instrument 5, are operated in this mode. Furthermore, the user can make adjustments, for example for changing the cutting power, by means of the input unit 19. To do so, one or more real adjustment devices can be provided on the surgical apparatus 13. To the extent that a user of the supply device wishes to change a parameter in terms of an active control, for example the RF voltage, the RF output, a time period or the like, the user can set a specific adjustment value by means of the adjustment device.

In order make the selection of a specific operating mode easier and to indicate status information regarding the RF generator 17 and/or the control unit 15 and/or the electrosurgical instrument 5, the supply device 1 can further include an output unit 21 that preferably includes a visual display unit for displaying information.

The control unit 15 can be in communicative connection with a memory unit 23 that comprises an interface 25. Via the interface 25, the configuration data can be loaded into the memory unit 23. The control unit 15 can include a time detecting unit 27 that pre-specifies sensor signals in the form of time signals, where such signals allow the detection of pre-specified time intervals.

The memory unit 23 can include a framework program to be executed by the control unit 15. This framework program causes the control unit 15 to load configuration data from the memory unit 23 and to generate a control program that enables the control of the instrument 5 connected to the supply device 1. Preferably, a table-controlled sequential circuit is implemented that can have a plurality of states $Z_0$ to $Z_x$, where the individual states $Z_0$ to $Z_x$ are adopted as a function of pre-specified boundary conditions.

The configuration data stored in the memory unit 23 model is preferably in table form, a finite state machine, or state automaton. A state automaton includes several states $Z_0$ to $Z_x$, wherein a transition can occur between the individual states due to transitions that describe a transition between a first and a second state. Each transition can be allocated at least one transition rule, also referred to as a state transition rule, where the rule contains at least one condition that, when fulfilled, changes the control unit 15 out of a control mode in accordance with the first state into a control mode in accordance with the second state. For example, a transition rule may include a condition that a transition into another state is executed only when the impedance R is greater than, e.g., 80 Ohm or the active power factor cos Φ is greater than 0.5. Furthermore, transition rules can require that a condition be maintained over a pre-specified period of time. In addition, it is possible that transition rules are implemented only when the active power factor cos Φ is greater than 0.5 for more than 5 milliseconds.

In accordance with the disclosed device, the supply device 1 can include a mediating unit that assigns at least one adjustment value of an actual or a virtual adjustment device to at least one mathematical function, said adjustment value having been received in the control unit 15 while the control program is being executed. The mediating unit corresponds more or less to an allocation device that is implemented in the control table or in the state automaton in the memory unit 23 and allocates one or more different mathematical functions to an adjustment device.

Considering the following example, the function of the supply device 1 is explained in relation to a situation where a user manually changes an adjustment value by means of a real adjustment device, namely, for example, a rotating knob or pushbutton of a surgical apparatus, while the control implements the state automaton:

In the present exemplary case, it is assumed that a user of the surgical apparatus 13 or the electrosurgical instrument 5 as in FIG. 1 wishes to change the cutting strength of the device. However, for safety reasons, preferably only a reduction of the cutting strength is possible. Preferably, for simplification, all adjustable values of an adjustment device can be normalized to values between 0 and 1. In doing so, the value 1 preferably corresponds to the maximum possible adjustment value of the adjustment device.

For example, an adjustment device $X_1$ has the initial adjustment value $x_1=0.7$, and a user changes the adjustment value of the adjustment device $x_1$ to 0.6. After the adjustment value has been changed, the real adjustment device thus reports an adjustment value of $x_1=0.6$. As soon as the adjustment device reports an adjustment value of $x_1=0.6$, the control searches for mediators in the mediating unit, said mediators being allocated to the adjustment device $X_1$. For example, it is possible that the adjustment device $X_1$ is referenced by two different mediators $V_1$ and $V_4$. Then, both mediators $V_1$ and $V_4$ allocate the adjustment value $x_1=0.6$ to two different mathematical functions 1 and 2, respectively, as shown in an exemplary manner as follows:

Mediator $V_1 \Rightarrow$ math. function 1: $y=Ax^2+Bx+C$; parameters: $A=0.5$; $B=0.5$; $C=0$ Target: State $Z_1$; Adjustment 1: $U\_HF$max→Scaling factor of the control value $Z_1.UHF$max is set to 0.68

Mediator $V_4 \Rightarrow$ math. function 2: $y=A*e^{Bx}+C$; parameters: $A=0.3$; $B=1$; $C=0$ Target: Jump 2A; waiting time→Scaling factor of the control value Trans 21.$TV$ is set to 0.55

Consequently, it becomes clear that the mediating unit, in principle, includes a list of several mediators $V_1$ through $V_x$, each allocating an adjustment device to a mathematical function. Several mediators can also allocate several functions to the same adjustment device, as is shown below with reference to the mediators $V_1$ and $V_2$, both performing an allocation of the adjustment device $X_1$, but to different functions. As follows, the principle of the function of the mediating unit is illustrated for clarification:

$V_1: X_1 \rightarrow F_1(x_1) \rightarrow Y_1$ $V_2: X_1 \rightarrow F_2(x_1) \rightarrow Y_2$ $V_3: X_2 \rightarrow F_3(x_2) \rightarrow Y_3$ $U_{Regulator} = Y_1 * U_{Setpoint}$ $P_{Regulator} = Y_2 * P_{Setpoint}$ $R_{Threshold} = Y_3 * R_{ThresholdOrg}$ It becomes clear that, for example, the mediator $V_1$ allocates a function $F_1$ to the adjustment device $X_1$ or to the adjustment value $x_1$ of the adjustment device $X_1$, and that another mediator $V_2$ of the mediating unit can allocate a second, different function $F_2$ to the same adjustment device $X_1$. A third mediator $V_3$, for example, can allocate a third different function $F_3$, but also one of the functions $F_1$ or $F_2$ or any other function, to another adjustment device $X_2$. Due to the option of allocation an adjustment device to several different mathematical functions by the mediating unit, several scaling factors $Y_1$ through $Y_x$ can be obtained by applying the adjustment values to the respective functions. In other words, a scaling factor Y is obtained in that an adjustment value x is inserted into a mathematical function F, whereby the link between the adjustment value and the correct function is determined by a mediator. In order to allow, for safety reasons, only a reduction of the existing control values, the function is preferably selected such that the resultant scaling factor assumes a value between 0 and 1.

The resultant scaling factors $Y_1$ through $Y_3$ can then be applied to different, freely selectable control values, as has been shown above in an exemplary manner with reference to the control values U (RF voltage), P (RF output) and R (Resistance). In other words, the obtained scaling factors are multiplied with control values, in which case the result produces the final control value that has to be pre-specified by the control unit.

Preferably, the scaling factors $Y_1$ through $Y_3$ are updated during a state transition from one state into another state of the state automaton. Thus, if during the execution of the control program a change of the adjustment value is made, there is a wait for the next state transition of the state automaton, because then the control table is recalculated by the control unit. Then, during the state transition, the adjustment value is inserted into the allocated function and the resultant scaling factor is calculated. Then, the scaling factor is multiplied with the allocated control value, thus finally resulting in the final control value to be set.

The mathematical functions may be any functions, for example square functions or exponential functions. One and the same adjustment value can be allocated to several different mathematical functions that, consequently, allocate different scaling factors to the adjustment value. Considering the above-stated example, it becomes clear that, in this manner, the same adjustment value $x_1=0.6$ can lead to different scaling factors for one voltage and one waiting time, e.g. to a scaling factor of 0.68 for the voltage U_HFmax and to a scaling factor of 0.55 for the waiting time Trans 21.TV. Consequently, by inserting the adjustment value $x_1$ into the function 1 and the function 2, two different scaling factors $Y_1$ and $Y_2$ are obtained. The "target" with which a scaling factor is to be ultimately multiplied is a specific, allocated control value that can be freely defined within the basic adjustment of the state automaton and/or in the states of the state automaton and/or in the jump conditions between the individual states.

However, manual actuation of an actual adjustment device by a user is not the only means to change an adjustment value; rather a new adjustment value of a virtual or actual adjustment device can also result from a tissue parameter and/or an RF measured value and, in general, from any sensor signal that is received or generated by the control unit 15, these acting as the parameters for transition rules or state transition rules during a jump from one state into another state of the state automaton. Thus, in this case, alternatively or in addition to the at least one actual adjustment device, a virtual adjustment device is provided, where the virtual adjustment device can include at least one simple control rule for a detected measured value or the like, whereby the results of the control rules are preferably again normalized to values between 0 and 1. Consequently, the results of the control rules form the adjustment values of the virtual adjustment device, whereby the control values, again, can be allocated to different real or virtual adjustment devices. The control rules can be determined when the state automaton is designed and can look, for example, as follows:

Initialize $x_4=4$
Initialize $x_5=0.3$

If jump 1A, then set $x_4$=2000 mA/IHFrms (normalization to 0 . . . 1)
If jump 1B, then set $x_4$=$x_4$+0.2
If jump 1C, then set $x_4$=0.3
If jump 2A, then set $x_5$=$x_5$*1.05
If jump 3A, then set $x_1$=$x_1$*0.2

The jumps 1A, 1B, etc., are transition rules that, if they are satisfied, trigger an action, in particular a jump from a first state into a second state, on the one hand, but also trigger an allocated control rule (as described above), on the other hand. For example, a state 1 of the state automaton can be defined as follows:

State 1: Start
→U_HFmax:=200 Vpeak
→I_HFmax:=3A rms
→P_HFmax:=120 W
Jump 1A>>>resistance exceeded<<<
Jump 1A: If 1 times RLast.=80 Ohm, then change to state: 3
Jump 1B>>>cos Φ<0.5 (=LF 16384)<<<
Jump 1B: If 50 times LF<16384, then change to state: 3
Jump 1C>>>time limit<<<
Jump 1C: If 10000 times, then change to state: 4

For example, if the transition rule 1A or the jump 1A has been satisfied, i.e., the resistance was exceeded, the control changes to state 2. However, in accordance with the invention, the true transition rule 1A not only triggers one transition state but, at the same time, leads to a change of an allocated adjustment value. Thus, if the transition rule 1A is satisfied, a control rule in the virtual adjustment device can be defined, for example, as shown above in that an adjustment device $X_4$ is set to an adjustment value $x_4$=2000 mA/IHFrms, wherein, again, a normalization of the resultant adjustment value $x_4$ takes place to a value between 0 and 1. If as opposed to this, the transition rule 1B is satisfied, i.e., the active power factor cos Φ is smaller than 0.5, then a control rule of the virtual adjustment device can effect an adjustment value of $x_4$=$x_4$+0.2 of the adjustment device $X_4$.

In this manner, different control rules can be allocated to different transition rules, said control rules—if satisfied—causing a change of an adjustment value of a virtual or a real adjustment device. Preferably, a single transition rule is allocated to a single control rule of the virtual adjustment device. However, it can also be intended that one transition rule is allocated to several control rules and, consequently, causes a change of several adjustment values of various adjustment devices.

The calculation of scaling factors on the basis of the new adjustment values and the different mathematical functions is then accomplished, by means of the allocation by mediators, as described above regarding the case of a real adjustment device.

The basic principle that is the foundation of the present invention shall be illustrated again with reference to the Table 1 (as follows):

TABLE 1

| Adjustment value = x = [0 . . . 1] | Function = y = [0 . . . 1] | Target |
|---|---|---|
| Real adjustment device (e.g., potentiometer or the like) | $y = Ax^2 + Bx + C$ | $U_{Regulator}$ = y * $U_{Setpoint}$ |
| R/$R_N$ | . | $P_{Regulator}$ = Y * $P_{Setpoint}$ |

TABLE 1-continued

| Adjustment value = x = [0 . . . 1] | Function = y = [0 . . . 1] | Target |
|---|---|---|
| .. | . | $R_{Threshold}$ = y * $R_{ThresholdOrg}$ |
| U/$U_N$ | $y = A * e^{Bx} + C$ | |
| | y = [0 . . . 1] | |

As a result of the disclosed device and method, it is possible for a user, during the implementation of the state automaton in the control unit 15, to dynamically affect the control values of the state automaton, on the one hand, and for the measured values or other parameters that are used for the transition rules to effect a change of the adjustment values by means of the control rules, on the other hand.

Overall, the mediating unit performs an allocation of an adjustment value of a real or a virtual adjustment device to a mathematical function, by means of which a scaling factor is obtained, said scaling factor effecting the scaling or change and, in particular, the reduction of a control value of the state automaton. In conjunction with this, the adjustment device is understood to mean a device that can effect a change of the adjustment values either by a manual measure performed by the user or by means of one or more control rules. Consequently, the adjustment device can be a "hardware element" or a "software element" of the supply device. It is decisive that said device perform a change of at least one adjustment value subsequent to a specific action.

A number of embodiments have been described. Nevertheless, it will be understood that various modifications may be made thereto without departing from the scope of the invention. It should also be understood that the appended drawings are not necessarily to scale, presenting a somewhat simplified representation of various preferred features illustrative of the basic principles of the invention. The invention should not be limited to any particular embodiment or feature disclosed, but is defined by the appended claims.

What is claimed is:

1. A supply device for a surgical apparatus for operating at least one surgical instrument, comprising:
    a memory unit for storing configuration data, the data comprising control values describing a state automaton having a plurality of states;
    a control unit for controlling the at least one surgical instrument, wherein the control unit is configured to read in the configuration data, translate the state automaton into a control program, and control the at least one surgical instrument consistent with the control program; and
    a mediating unit having at least one mediator for allocating at least one adjustment value of at least one of an actual adjustment device and a virtual adjustment device to a mathematical function to obtain a scaling factor for a control value, the adjustment value being received during the execution of the control program, wherein the virtual adjustment device comprises at least one control rule for at least one transition between two states of the state automaton.

2. The supply device of claim 1, wherein the actual adjustment device can be actuated by a user of a surgical apparatus.

3. The supply device of claim 1, wherein a result of the control rule forms the adjustment value of the virtual adjustment device.

4. The supply device of claim 1, wherein the scaling factor is used to reduce the control value.

5. The supply device of claim 1, wherein several mathematical functions are allocated by the mediating unit to an adjustment value, said functions generating scaling factors for the adaptation of different control values.

6. The supply device of claim 1, wherein the adjustment value of the actual adjustment device or the virtual adjustment device is between 0 and 1.

7. The supply device of claim 1, wherein the mediating unit comprises a list with a plurality of mediators.

8. The supply device of claim 1, wherein the surgical instrument is selected from the group consisting of an electrosurgical instrument, a cryogenic instrument, and a waterjet instrument.

9. A method of generating a control program for a supply device of at least one surgical instrument, said method comprising:
reading-in configuration data that describe a state automaton displaying a plurality of states;
translating the state automaton displaying the plurality of states into a control program by means of a control unit;
controlling the at least one surgical instrument with the control unit consistent with the control program;
receiving at least one adjustment value of at least one of an actual adjustment device and a virtual adjustment device;
calculating at least one scaling factor using the adjustment value and at least one allocated mathematical function; and
changing at least one allocated control value based on the scaling factor, wherein the virtual adjustment device comprises at least one control rule for at least one transition between two states of the state automaton.

10. The method of claim 9, wherein the control unit searches for at least one allocated function following the receipt of the adjustment value.

11. The method of claim 9, wherein the scaling factors are updated during a transition from one state to the other state of the state automaton.

12. The supply device of claim 7, wherein each of the plurality of mediators is associated with a different function and a different control value.

13. The method of claim 9, wherein the calculating step comprises calculating a plurality of scaling factors using the adjustment value and a plurality of allocated mathematical functions, and the changing step comprises changing a plurality of allocated control values based on the respective scaling factor.

* * * * *